(12) United States Patent
Chandrashekhar et al.

(10) Patent No.: US 11,154,498 B2
(45) Date of Patent: Oct. 26, 2021

(54) STABILIZED LIQUID FORMULATION OF LEVOTHYROXINE

(71) Applicant: Leiutis Pharmaceuticals PVT. LTD., Hyderabad (IN)

(72) Inventors: Kocherlakota Chandrashekhar, Secunderabad (IN); Banda Nagaraju, Hyderabad (IN)

(73) Assignee: Leiutis Pharmaceuticals PVT. LTD., Hyderabad (IN)

( * ) Notice: Subject to any disclaimer, the term of this patent is extended or adjusted under 35 U.S.C. 154(b) by 0 days.

(21) Appl. No.: 15/745,615

(22) PCT Filed: Jul. 20, 2016

(86) PCT No.: PCT/IB2016/054308
§ 371 (c)(1),
(2) Date: Jan. 17, 2018

(87) PCT Pub. No.: WO2017/013591
PCT Pub. Date: Jan. 26, 2017

(65) Prior Publication Data
US 2018/0214374 A1 Aug. 2, 2018

(30) Foreign Application Priority Data
Jul. 22, 2015 (IN) .......................... 3770/CHE/2015

(51) Int. Cl.
| | | |
|---|---|---|
| *A61K 9/08* | (2006.01) |
| *A61K 31/198* | (2006.01) |
| *A61K 9/00* | (2006.01) |
| *A61K 31/197* | (2006.01) |
| *A61K 47/02* | (2006.01) |
| *A61K 47/10* | (2017.01) |
| *A61K 47/18* | (2017.01) |
| *A61K 47/40* | (2006.01) |

(52) U.S. Cl.
CPC .............. *A61K 9/08* (2013.01); *A61K 9/0019* (2013.01); *A61K 31/197* (2013.01); *A61K 31/198* (2013.01); *A61K 47/02* (2013.01); *A61K 47/10* (2013.01); *A61K 47/183* (2013.01); *A61K 47/40* (2013.01)

(58) Field of Classification Search
CPC ................................ A61K 9/08; A61K 31/197
See application file for complete search history.

(56) References Cited

U.S. PATENT DOCUMENTS

| | | | |
|---|---|---|---|
| 2,889,363 A | 6/1959 | Ginger et al. | |
| 2,889,364 A | 6/1959 | Ginger et al. | |
| 5,635,209 A * | 6/1997 | Groenewoud | A61K 9/2009 424/464 |
| 5,856,359 A * | 1/1999 | Fischer | A61K 9/7061 514/567 |
| 5,955,105 A | 9/1999 | Mitra et al. | |
| 6,056,975 A | 5/2000 | Mitra et al. | |
| 7,648,702 B2 * | 1/2010 | Gombotz | A61K 9/0019 424/134.1 |
| 9,006,289 B2 | 4/2015 | Jiang et al. | |
| 2006/0034778 A1 * | 2/2006 | Kitano | A61Q 5/02 424/47 |
| 2009/0105314 A1 * | 4/2009 | Li | A61P 43/00 514/359 |
| 2009/0270507 A1 * | 10/2009 | Pierres | A61K 9/0095 514/567 |
| 2011/0207764 A1 * | 8/2011 | Alakhov | A61K 9/0019 514/283 |
| 2014/0073965 A1 | 3/2014 | Psarrakis et al. | |

FOREIGN PATENT DOCUMENTS

| | | | |
|---|---|---|---|
| WO | WO 2004/060353 A1 | 7/2004 |
| WO | WO 2007/077252 A1 | 7/2007 |
| WO | WO2007077252 A1 * | 7/2007 |
| WO | WO 2011/104625 A1 | 9/2011 |

OTHER PUBLICATIONS

McGraw Hill Higher Education (Chapter 27: Amino Acids, Peptides and Protein (2014) pp. 1-2) [online] Retrieved from the internet, [Retrieved on Jul. 25, 2018], <url:http://www.mhhe.com/physsci/chemistry/carey5e/Ch27/ch27-1-4-2.html> (Year: 2014).*
Hirano et al. J. Phys. Chem. B (2010), vol. 114, pp. 13455-13462 (Year: 2010).*
Ueda et al. Drug Development and Industrial Pharmacy, (1998), vol. 24, pp. 863-867 (Year: 1998).*
PubChem CID5819 [online] Retrieved on: Sep. 26, 2019, Created by: Sep. 2004 <url: https://pubchem.ncbi.nlm.nih.gov/compound/Levothyroxine#section=Melting-Point> (Year: 2004).*
Ariki et al. (J. Biochem (2011), vol. 149, pp. 389-394) (Year: 2011).*
International Search Report and Written Opinion dated Jan. 13, 2017 for International Application No. PCT/IB2016/056615, 8 pages.
International Search Report and Written Opinion dated Nov. 25, 2016 for International Application No. PCT/IB2016/054308, 8 pages.

* cited by examiner

Primary Examiner — Taina D Matos Negron
(74) Attorney, Agent, or Firm — Heslin Rothenberg Farley & Mesiti P.C.

(57) ABSTRACT

The present invention relates to stabilized liquid formulations of Levothyroxine or a pharmaceutically acceptable salt thereof, intended for parenteral administration. Further this invention also describes process of preparing such compositions.

10 Claims, No Drawings

STABILIZED LIQUID FORMULATION OF LEVOTHYROXINE

BACKGROUND OF THE INVENTION

Thyroxine active drugs are known for both therapeutic and prophylactic treatment of thyroid disorders. The thyroid accomplishes its regulation functions by producing the hormones L-triiodothyronine (liothyronine; T3) and L-thyroxine (levothyroxine; T4). The physiological actions of thyroid hormones are produced predominantly by T3, the majority of which (approximately 80%) is derived from T4 by deiodination in peripheral tissues.

Administration of levothyroxine sodium provides T4 to a patient. Once absorbed, the administered T4 behaves identically to T4 that otherwise would be secreted by the thyroid gland of the patient, and binds to the same serum proteins, providing a supply of circulating T4-thyroglobulin in the patient. The administered T4 may be deiodinated in vivo to T3. As a result, a patient receiving appropriate doses of levothyroxine sodium will exhibit normal blood levels of T3, even when the patient's thyroid gland has been removed or is not functioning.

Levothyroxine sodium is prescribed for thyroid hormone replacement therapy in cases of reduced or absent thyroid function e.g., ailments such as myxedema, cretinism and obesity. Levothyroxine sodium is quite unstable, hygroscopic and degrades rapidly when subjected to high humidity, light or high temperature. Because of the physicochemical properties of the drug, formulations of levothyroxine sodium have extremely short stability duration, worsened under conditions of high humidity and temperature.

Levothyroxine sodium is available in the form of capsules, tablets and parenteral dosage forms. Levothyroxine sodium for injection is available as sterile lyophilized product for parenteral administration containing 100 mcg/vial, 200 mcg/vial and 500 mcg/vial.

Conventional formulations of levothyroxine sodium for injection are preservative-free lyophilized powders containing synthetic crystalline levothyroxine sodium, mannitol, tribasic sodium phosphate, and sodium hydroxide. These conventional formulations typically contain 10 mg mannitol, 700 μg of tribasic sodium phosphate and 100 mcg or 200 mcg or 500 mcg of levothyroxine sodium. Administration of the conventional formulation involves reconstitution of the lyophilized powder in 5 mL of 0.9% sodium chloride injection, to provide injectable solutions having levothyroxine sodium concentrations of 20 mcg/mL, 40 mcg/mL or 100 mcg/mL.

U.S. Pat. No. 9,006,289, issued on Apr. 14, 2015, to Jiang, et al., discloses lyophilized composition comprising of levothyroxine sodium, a phosphate buffer and mannitol.

Levothyroxine has extremely short stability, worsened under conditions of high humidity and temperature. Due to this instability, Levothyroxine injectable formulations are used in the form of lyophilized formulations that are dissolved in 0.9% sodium chloride Injection immediately before injection. The present inventors have developed stable liquid formulations of Levothyroxine intended for parenteral administration.

SUMMARY OF THE INVENTION

One object of the invention provides stable liquid parenteral pharmaceutical formulation of Levothyroxine.

Another aspect of the invention provides stable liquid parenteral pharmaceutical formulation of Levothyroxine comprising Levothyroxine, buffering agents, one or more solvents and other pharmaceutically acceptable excipients thereof.

Yet another aspect of the invention provides liquid parenteral pharmaceutical formulation of Levothyroxine comprising Levothyroxine sodium, buffering agents, stabilizing agents, one or more solvents and other pharmaceutically acceptable excipients thereof.

DETAILED DESCRIPTION OF THE INVENTION

The present invention relates to stable liquid parenteral formulation of Levothyroxine, and more particularly to stable Levothyroxine liquid formulation comprising of buffering agents, stabilizing agents, solvents and other pharmaceutically acceptable excipients thereof.

In the context of this invention "Levothyroxine" refers to the pharmaceutically acceptable salts, solvates, hydrates and anhydrous forms thereof. The formulations of the present invention preferably comprise Levothyroxine sodium.

As used herein, "liquid parenteral formulations of Levothyroxine" refers to formulations that contain Levothyroxine in dissolved or solubilised form and are intended to be used as such or upon dilution in intravenous diluents.

Levothyroxine sodium is quite unstable, hygroscopic and degrades rapidly when subjected to high humidity, light or high temperature. Degradation is further enhanced by the presence of water. Hence, attempts to develop an intravenous preparation of Levothyroxine were limited.

The inventors of the present invention have surprisingly found that it is possible to develop stable liquid parenteral pharmaceutical formulation of Levothyroxine, despite its rapid degrading nature.

One embodiment of the invention relates to liquid parenteral pharmaceutical formulations of Levothyroxine comprising:
  i. Levothyroxine
  ii. buffering agents
  iii. one or more solvents and
other pharmaceutically acceptable excipients thereof.

Yet another embodiment of the invention relates to liquid parenteral pharmaceutical formulation of Levothyroxine comprising:
  i. Levothyroxine sodium
  ii. buffering agents,
  iii. stabilizing agents and/or solubilizing agents
  iv. one or more solvents and
  v. optionally one or more pharmaceutically acceptable excipients selected from pH adjusting agents and antioxidants.

Stabilizing agents used in the formulation include, but not limited to sodium iodide, potassium iodide and the like. The pharmaceutical compositions of the present invention may also contain solubilizing agents such as cyclodextrins. These agents may be used in the formulation to maintain the solubility and stability of levothyroxine sodium during the entire shelf life of the formulation. Suitable cyclodextrins include but not limited to α, β and γ-cyclodextrin and cyclodextrins modified with alkyl-, hydroxyalkyl-, dialkyl-, and sulfoalkyl-ether modified cyclodextrins such as methyl or hydroxypropyl β-cyclodextrins (HPβCD), methyl-and-ethyl-β-cyclodextrin, sulfoalkylether-substituted beta-cyclodextrin, sulfobutylether-β-cyclodextrin (SBECD) and the like.

Suitable buffering agents include amino acids such as arginine, alanine, histidine, glycine and lysine; citrate, glutamate, bicarbonate, tartrate, benzoate, lactate, gluconate, TRIS, acetate, meglumine, borate and phosphate buffer.

Suitable solvents include, but not limited to dimethylacetamide, dimethyl sulfoxide, N-methylpyrrolidone, dimethylisosorbide, ethanol, propylene glycol, polyethylene alcohol, propylene glycol esters, polyethylene glycols, glycerine, water and the like. Preferred solvents are water and propylene glycol.

Suitable pH adjusting agents include sodium hydroxide, sodium carbonate, sodium bicarbonate, potassium hydroxide, ammonium carbonate, hydrochloric acid, citric acid, lactic acid, phosphoric acid, sodium phosphate, sulfuric acid and the like.

The pharmaceutical compositions of the present invention may also contain one or more anti-oxidants such as sodium sulfite, sodium bisulfite, sodium metabisulfite, sodium thiosulphate, sodium formaldehyde sulfoxylate, citric acid, tocopherol, butylated hydroxy anisole, butylated hydroxy toluene, monothioglycerol, ascorbic acid, sodium ascorbate and propyl gallate.

The inventors carried out experiments with various buffering agents to determine suitable buffering agent in the final formulation. Levothyroxine formulations prepared were tested for stability at 60±2° C. (3 days). The data is summarized in table 1.

TABLE 1

Evaluation of different buffering agents for their suitability in the formulation.

| Ingredients | Quantity in mg | | | | | |
|---|---|---|---|---|---|---|
| | A1 | A2 | A3 | A4 | A5 | A6 |
| Levothyroxine sodium | 0.05 | 0.05 | 0.05 | 0.05 | 0.05 | 0.5 |
| Arginine | 10 | — | — | — | — | — |
| Sodium carbonate buffer | — | 10 | — | — | — | — |
| Sodium hydrogen carbonate buffer | — | — | 10 | — | — | — |
| Tris buffer | — | — | — | 8 | — | — |
| Tri basic sodium phosphate dodeca hydrate buffer | — | — | — | — | 2.3 | — |
| Meglumine buffer | — | — | — | — | — | 1 |
| Mannitol | 1.5 | 1.5 | 1.5 | 1.5 | 1.5 | — |
| Sodium hydroxide | q.s to adjust the pH 11.0 ± 1.0 | | | | | |
| Water for Injection | Qs to 1 ml | | | | | |
| Observations 60 ± 2° C. (3 days) | | | | | | |
| Total impurities | 3.14 | 5.49 | 6.42 | 5.82 | 11.99 | 4.8 |

A preferred embodiment of the invention relates to liquid parenteral pharmaceutical formulation of Levothyroxine comprising:
  i. Levothyroxine sodium
  ii. stabilizing agents and/or solubilizing agents selected from sodium iodide, potassium iodide and cyclodextrins
  iii. buffering agent(s) selected from aminoacids such as arginine, alanine, histidine, glycine and lysine; citrate, glutamate, bicarbonate, tartrate, benzoate, lactate, gluconate, TRIS, acetate, borate and phosphate buffer
  iv. one or more solvents selected from the group comprising water, polyethylene glycol, ethanol, propylene glycol and glycerine
  v. optionally one or more pharmaceutically acceptable excipients selected from pH adjusting agents and anti-oxidants.

Levothyroxine formulation prepared according to the invention was tested for stability at 2-8° C., 25° C. and 60° C. for a period of 1 month. The stability data of the invention formulation is summarized in table 2.

TABLE 2

Stability data of the product prepared according to example 5 Levothyroxine sodium Invention formulation stability data

| Storage condition | 2-8° C. | 2-8° C. | 25° C. | 25° C. | 60° C. | 60° C. |
|---|---|---|---|---|---|---|
| Storage duration | 1 week | 1 month | 1 week | 1 month | 1 week | 1 month |
| Total impurities | 0.39 | 0.50 | 0.43 | 0.55 | 0.58 | 1.10 |
| pH | 6.25 | 6.40 | 6.67 | 6.81 | 6.21 | 6.47 |
| Osmolality (mOsm/kg) | 272 | 255 | 263 | 238 | 266 | 262 |

Surprisingly no significant increase in impurities was observed even at accelerated conditions. The data confirms the inventors' finding that Levothyroxine formulations in the presence of suitable excipients resulted in a stable product.

The following examples further describe certain specific aspects and embodiments of the present invention and demonstrate the practice and advantages thereof. It is to be understood that the examples are given by way of illustration only and are not intended to limit the scope of the invention in any manner.

Example 1

| Ingredients | Quantity |
|---|---|
| Levothyroxine sodium | 0.01-1 mg |
| Arginine | 0.01-4 mg |
| Propylene glycol | 0.01-1 ml |
| Sodium hydroxide | qs |
| Water for injection | Qs to 0.1-2 ml |

Manufacturing Process

Water for injection was taken in a compounding vessel and arginine was added and stirred. Propylene glycol was added to the above solution and stirred. Then the bulk solution was cooled to 2° C. to 8° C. Levothyroxine sodium was added and stirred till a clear solution was obtained, while maintaining the temperature at 5±3° C. pH of the solution was adjusted to 11±1.0 by the addition of sodium hydroxide solution. The solution was filtered, followed by stoppering and sealing of the vials.

Example 2

| Ingredients | Quantity |
|---|---|
| Levothyroxine sodium | 0.01-1 mg |
| Alanine | 0.006-4 mg |
| Propylene glycol | 0.01-1 ml |
| Sodium hydroxide | qs |
| Water for injection | Qs to 0.1-2 ml |

Manufacturing Process

Water for injection was taken in a compounding vessel and alanine was added and stirred. Propylene glycol was added to the above solution and stirred. Then the bulk solution was cooled to 2° C. to 8° C. Levothyroxine sodium was added and stirred till a clear solution was obtained, while maintaining the temperature at 5±3° C. The solution was filtered, followed by stoppering and sealing of the vials.

Example 3

| Ingredients | Quantity |
| --- | --- |
| Levothyroxine sodium | 0.01-1 mg |
| L-Arginine | 250 mcg |
| Sodium acetate anhydrous | 10500 mcg |
| Potassium hydroxide | 1500 mcg |
| Sodium metabisulfite | 500 mcg |
| Sodium iodide | 1000 mcg |
| Water for injection | Qs to 0.1-6 ml |

Manufacturing Process

L-Arginine was added to the manufacturing vessel containing water for injection, sodium acetate anhydrous was added to the above solution and stirred well. Potassium hydroxide was added to the above solution followed by the addition of sodium metabisulfite and sodium iodide. The solution was cooled to 2-8° C. Levothyroxine sodium was added to the above solution and stirred till a homogeneous solution was obtained.

Example 4

| Ingredients | Quantity |
| --- | --- |
| Levothyroxine sodium | 0.01-1 mg |
| Arginine | 250 mcg |
| Sodium acetate anhydrous | 10500 mcg |
| Potassium hydroxide | 1500 mcg |
| Sodium iodide | 1000 mcg |
| Water for injection | Qs to 0.1-6 ml |

Manufacturing Process

Arginine was added to the manufacturing vessel containing water for injection, sodium acetate anhydrous was added to the above solution and stirred well. Potassium hydroxide was added to the above solution followed by the addition of sodium iodide.

The solution was cooled to 2-8° C. Levothyroxine sodium was added to the above solution and stirred till a homogeneous solution was obtained.

Example 5

| Ingredients | Quantity |
| --- | --- |
| Levothyroxine sodium | 0.01-1 mg |
| Arginine | 0.05 mg |
| Sulfobutylether-β-cyclodextrin (SBECD) | 83.9 mg |
| Sodium iodide | 2.00 mg |
| Water for injection | Qs to 0.1-3 ml |

Brief Manufacturing Process

SBECD was added to the manufacturing vessel containing water for injection followed by the addition of Levothyroxine sodium. Arginine was added and stirred well, till a clear solution was obtained. Sodium iodide was added to the above solution. The pH of the solution was adjusted to 6.0±1.0 (if necessary) with sodium hydroxide/hydrochloric acid.

We claim:

1. A stable, liquid parenteral pharmaceutical formulation of levothyroxine comprising:
   (i) levothyroxine sodium in a concentration of less than 0.1% w/v;
   (ii) a solubilizing agent comprising a cyclodextrin;
   (iii) optionally one or more stabilizing agents;
   (iv) arginine in a concentration of less than 0.20 M; and
   (v) one or more solvents, wherein the pH is between 5 and 7.

2. The liquid parenteral pharmaceutical formulation of claim 1, wherein the stabilizing agents are selected from one or both sodium iodide and potassium iodide.

3. The liquid parenteral pharmaceutical formulation of claim 1 wherein the cyclodextrin is sulfobutylether-β-cyclodextrin (SBECD).

4. The liquid parenteral pharmaceutical formulation of claim 1, wherein the solvent is water.

5. The liquid parenteral pharmaceutical formulation of claim 1, wherein the solvent is propylene glycol.

6. The liquid parenteral pharmaceutical formulation of claim 1, wherein the pH of the formulation is 6.

7. The liquid parenteral pharmaceutical formulation of claim 1, wherein the cyclodextrin is selected from α, β and γ-cyclodextrin and cyclodextrins modified with alkyl-, hydroxyalkyl-, dialkyl-, and sulfoalkyl-ether modified cyclodextrins.

8. A stable, liquid parenteral pharmaceutical formulation of levothyroxine comprising:
   (i) levothyroxine sodium;
   (ii) sulfobutylether-β-cyclodextrin (SBECD)
   (iii) arginine in a concentration of less than 0.20 M; and
   (iv) one or more solvents, wherein the pH is between 5 and 7.

9. The liquid parenteral pharmaceutical formulation of claim 8, wherein the pH of the formulation is 6.

10. The liquid parenteral pharmaceutical formulation of claim 8, wherein arginine is in a concentration between approximately 0.06M to approximately 0.0001M.

* * * * *